United States Patent [19]

Veber

[11] 4,140,767

[45] Feb. 20, 1979

[54] SOMATOSTATIN ANALOGS

[75] Inventor: Daniel F. Veber, Ambler, Pa.

[73] Assignee: Merck & Co., Inc., Rahway, N.J.

[21] Appl. No.: 856,376

[22] Filed: Dec. 1, 1977

[51] Int. Cl.$^2$ .................... A61K 37/00; C07C 103/52
[52] U.S. Cl. ............................ 424/177; 260/112.5 S
[58] Field of Search .................. 260/112.5 S; 424/177

[56] References Cited

U.S. PATENT DOCUMENTS 3,997,517  12/1976  Sarantakis ................. 260/112.5 S

OTHER PUBLICATIONS

Sarantakis et al., Biochem. Biophys. Res. Comm., 75, 143-148 (1977).

*Primary Examiner*—Delbert R. Phillips
*Attorney, Agent, or Firm*—Walter Patton; Harry E. Westlake, Jr.

[57] ABSTRACT

Bicyclic somatostatin analogs and pharmaceutically acceptable non-toxic acid addition salts thereof are prepared by the solid phase method. These analogs have the property of inhibiting the release of growth hormone without affecting the level of gastric secretions or without affecting the level of gastric secretions, insulin and glucagon in humans and animals. The compounds are particularly useful in the treatment of acromegaly and diabetic retinopathy. Due to the bicyclic structure, these analogs are resistant to enzymatic metabolism and have a longer duration of activity than somatostatin.

3 Claims, No Drawings

SOMATOSTATIN ANALOGS

BACKGROUND OF THE INVENTION

Somatostatin is a tetradecapeptide having the structure:

and has the properties of inhibiting the release of growth hormone, inhibiting the release of insulin and glucagon and reducing gastric secretion. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself.

The present invention provides bicyclic somatostatin analogs which preferentially inhibit the release of growth hormone without affecting the level of gastric secretions or without affecting the level of gastric secretions, insulin and glucagon and thus have a more selective biological activity than somatostatin. The present analogs also have a longer duration of action than somatostatin because of their bicyclic structure. The present invention provides a novel method for preparing said analogs.

SUMMARY OF THE INVENTION

This invention is concerned with novel bicyclic somatostatin analogs having a more selective biological activity and a longer duration of action than naturally occurring somatostatin and having the structural formula:

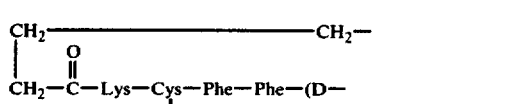

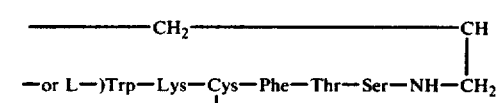

and pharmaceutically acceptable non-toxic acid addition salts thereof.

Illustrative of acid addition salts are hydrochloride, hydrobromide, sulfate, phosphate, meleate, acetate, citrate, benzoate, succinate, malate, ascorbate and the like. The acid addition salts can be conveniently prepared by dissolving the above novel compounds in water, adding two equivalents of appropriate acid and lyophilizing.

Included in the present invention are the monocyclic (Acm)Cys containing intermediates having the structural formula:

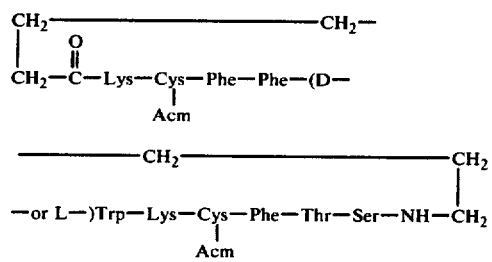

The bicyclic somatostatin analogs of the present invention differ from somatostatin by virtue of the fact that they have a covalent bond between the side chains of two amino acids within the macrocyclic ring. This novel feature can be illustrated by reference to the structure of somatostatin.

Somatostatin is a tetradecapeptide having the structure:

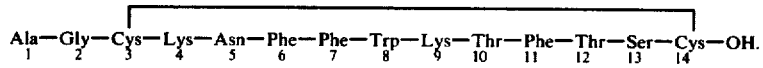

The portion of somatostatin extending from amino acid $Cys^3$ to $Cys^{14}$ forms a cyclic dodecapeptide of the following structure:

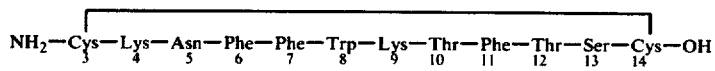

This cyclic dodecapeptide is referred to as the macrocyclic ring of somatostatin. The macrocyclic ring of the compounds of the present invention are illustrated by the following structural formula:

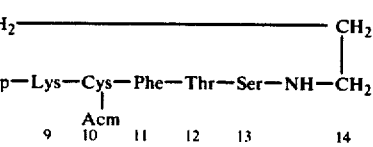

Whereas, in somatostatin positions 3 and 14 are bridged by cystine, the present invention provides somatostatin analogs wherein positions 3 and 14 are bridged by 7-aminoheptanoic acid. Accordingly, the disulfide atoms of somatostatin have been replaced by the dicarba group, —CH$_2$—CH$_2$—. This forms the macrocyclic ring of the bicyclic somatostatin analogs of the present invention, which will hereinafter be referred to as Ring I. The removal of the Acm protecting groups from the Cys amino acids within the macrocyclic ring followed by oxidation of the sulfhydryl group results in formation of Rings II and III. The ring structure formed by amino acids 6 to 9 of Ring I and the side groups of amino acids 5 and 10 joined by a disulfide bond is designated Ring II. The amino acids at position 6 to 9 of Ring I are common to both Rings I and II. The ring structure formed by the amino acids of Ring I (not commonly shared by Ring I and II) and the side groups of amino acids 5 and 10 joined by a disulfide bond is designated Ring III.

In the bicyclic somatostatin analogs of the present invention Ala$^1$-Gly$^2$, the amino group of Cys$^3$ and the carboxylic acid group of Cys$^{14}$ of somatostatin are deleted.

Furthermore, the bicyclic somatostatin analogs of the present invention include those wherein Trp$^8$ is replaced by D-Trp.

The bicyclic somatostatin analogs of the present invention differ from somatostatin by virtue of the fact that they lack an N-terminal amino group thus eliminating the group involved in enzymic cleavage of the molecule by aminopeptidases. Further stability is attained by the formation of Rings II and III as described above. The presence of these rings increases the rigidity of the molecule and reduces its susceptibility to enzymatic metabolism. Generally, very few peptidases cleave peptides at cystine residues. Therefore, the analogs of the present invention are more resistant to cleavage in vivo than somatostatin and thus have a prolonged duration of action.

The abbreviated designations, which are used herein for the amino acid components, certain preferred protecting groups, reagents and solvents employed in the process of this invention are as follows:

TABLE I

| Abbreviated Designation | Amino Acid |
|---|---|
| Lys | L-lysine |
| Phe | L-phenylalanine |
| Trp | L-tryptophan |
| D—Trp | D-tryptophan |
| Thr | L-threonine |
| Aha | 7-aminoheptanoic acid |
| Tyr | L-tyrosine |
| Val | L-valine |
| Abu | L-α-aminobutyric acid |
| Ser | L-serine |
| Asn | L-asparagine |
| Pro | L-proline |
| Asu | D- or L-aminosuberic acid |
| Cys | L-cysteine |
| Abbreviated Designation | Protecting Groups |
| INOC | isonicotinyloxycarbonyl |
| BOC | tert-butyloxycarbonyl |
| OMe | methyl ester |
| tBu | tert-butyl |
| CBZ | benzyloxycarbonyl |
| Bzl | benzyl |
| 2-Cl-CBZ | 2-chlorobenzyloxycarbonyl |
| Acm | acetamidomethyl |
| Abbreviated | Activating |

TABLE I-continued

| Abbreviated Designation | Amino Acid |
|---|---|
| Designation | Groups |
| ONp | p-nitrophenyl ester |
| HSE | N-hydroxysuccinimide ester |
| HBT | 1-hydroxybenzotriazole |
| Abbreviated | Condensing |
| Designation | Agents |
| DCCI | dicyclohexylcarbodiimide |
| Abbreviated Designation | Reagents |
| TFA | trifluoroacetic acid |
| TEA | triethylamine |
| DIPEA | diisopropylethylamine |
| Abbreviated Designation | Solvents |
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

DESCRIPTION OF THE PREFERRED EMBODIMENTS

In accordance with the present invention, Ring I of the novel bicyclic somatostatin analogs is prepared by cyclizing corresponding linear peptides. The linear peptides are prepared by using the solid phase sequential synthesis technique. Accordingly, the process for preparing Ring I of the bicyclic somatostatin analogs of the present invention comprises a) preparing a corresponding blocked linear peptide attached to a solid phase resin; b) selectively deblocking the N-terminal amine group; c) removing the linear peptide from the resin; d) treating the linear peptide with a cyclizing agent to obtain Ring I of the bicyclic peptide through the formation of an amide bond.

Rings II and II are formed by removing the remaining blocking groups and oxidizing the sulfhydryl groups of Cys within the macrocyclic Ring I. The bicyclic structure is thereby generated through the formation of the disulfide bond. The relative location of the Cys amino acids in Ring I determines the location and size of Rings II and III.

When the linear peptide is prepared on the resin, it is not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide. As an example to illustrate this, either of the two following linear peptides, when cyclized, will give the identical Ring I of the bicyclic somatostatin analog:

D—Trp—(ε-2-Cl—CBZ)Lys—(Acm)Cys—Phem(O—Bzl)Thr—(O—Bzl)Ser—Aha—(ε-2-Cl—CBZ)Lys—(Acm)Cys—Phe—Phe—N$_3$
Aha—(ε-2-Cl—CBZ)Lys—(Acm)Cys—Phe—Phe—D—Trp—(ε-2-Cl—CBZ)-Lys—(Acm)Cys—Phe—(O—Bzl)Thr—(O—Bzl)Ser—N$_3$
cyclization
cyclo[Aha—(ε-2-Cl—CBZ)Lys—(Acm)Cys—Phe—Phe—D—Trp—(ε-2-Cl—CBZ)Lys—(Acm)Cys—Phe—(O—Bzl)Thr—(O—Bzl)Ser].

It is evident that since the linear peptide is going to be cyclized, it does not matter which amino acid is used to start the chain. Starting with Phe at the carboxyl end, as illustrated in the first of the two examples above, has an advantage over the second example. In the first example, D-Trp, which can react with t-butyl carbonium ions formed when BOC groups are removed, is the N-terminal amino acid and thus will be added last and hence will be subjected to the least amount of exposure to t-butyl carbonium ions.

The synthesis of the linear peptides by the solid phase technique is conducted in a stepwise manner on chloromethylated resin. The resin is composed of fine beads (20-70 microns in diameter) of a synthetic resin prepared by copolymerization of styrene with 1 to 2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e., trifluoro acetic acid, or hydrogen chloride in ethyl acetate).

The —OH group of Thr and Ser can be protected by the Bzl group and the ε-amino group of Lys can be protected by the INOC group or the 2-chlorobenzyloxycarbonyl (2-Cl-CBZ) group. In the case of Lys, it is preferred to protect the ε-amino group with 2-Cl-CBZ group as this group is removed simultaneously with the Bzl groups by treatment with HF after the linear peptide has been cyclized. The INOC group is not removed by HF and requires an additional treatment with Zn. Neither group is affected by TFA, used for removing BOC protecting groups.

The sulfhydryl group of Cys is protected by Acm. After the linear peptide is cyclized to form Ring I, the protective groups, such as 2-Cl-CBZ and Bzl, are removed by treatment with HF. A particular advantage in using the Acm group is that, it is stable to HF and therefore remains intact after the formation of Ring I and before the formation of Rings II and III. This allows the purification of the intermediate monocyclic compound prior to removal of the Acm group and oxidation of the sulfhydryl groups to form Rings II and III.

After the linear peptide has been formed on the solid phase resin, it may be removed from the resin by a variety of methods which are well known in the art. For example, the peptide may be cleaved from the resin with hydrazine and thus directly form the peptide hydrazide which may be subsequently cyclized via the azide to the desired Ring I of the bicyclic peptide. The hydrazide is converted to the corresponding azide by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, etc. This reaction is carried out in the presence of either water and/or a non-aqueous solvent such as dimethylformamide, tetrahydrofuran, dioxane, chloroform, methylene chloride, etc., at a temperature between about −40° C. and +20° C. Alternatively, the peptide may be removed from the resin by treatment with a lower alcohol such as methanol in the presence of an organic base such as triethylamine, thus resulting in the formation of the corresponding lower alcohol ester of the linear peptide. The resulting ester may be converted to the hydrazide which may then be cyclized, via the azide, to the desired Ring I of the bicylic peptide. The preferred method for cleaving the peptide from the resin in the present invention is the use of hydrazine.

Rings II and III of the bicyclic somatostatin analogs are formed by removing the Acm protecting group from the sulfhydryl groups of Cys and oxidizing the sulfhydryl groups to disulfide. This is accomplished by $I_2$ in acetic acid or alternately by mercuric ion followed by air oxidation.

As reference to Table II will show, one preferred overall procedure for preparing the desired bicyclic peptides of the present invention involves the stepwise synthesis of the linear peptide on a solid phase resin. More specifically, in the process for preparing:

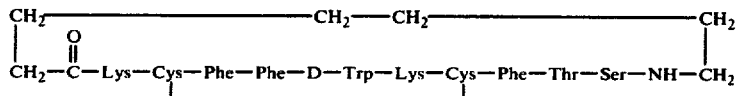

the carboxyl end of the N-blocked amino acid phenylalanine is bound covalently to an insoluble polymeric resin support as the carboxylic acid ester of the resin-bonded benzyl chloride. The amino group of Phe is protected by the BOC group. After the attachment of the Phe is completed on the resin, the protecting group BOC is removed by treatment with TFA in $CH_2Cl_2$. The subsequent amino acids are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence:

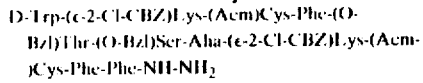

is treated with isoamyl nitrite in acid pH to form the corresponding azide. The azide solution is diluted with solvent and neutralized with an organic base. The linear peptide cyclizes to form Ring I, i.e. cyclo[Aha-(ε-2-Cl-CBZ)Lys-(Acm)Cys-Phe-Phe-D-Trp-(ε-2-Cl-CBZ)Lys-(Acm)Cys-Phe-(O-Bzl)Thr-(O-Bzl)Ser]. During the cyclization the "pH" is checked and maintained at neutral by the addition of organic base. The "pH" in organic solvent is determined by the application of an aliquot of the solution to moistened narrow range pH paper.

After the linear peptide is cyclized to form Ring I, the protective groups, 2-Cl-CBZ and Bzl, are removed by treatment with HF in the presence of anisole. The crude cyclic peptide obtained is purified by chromatography, preferably on Sephadex eluted with 50% aqueous acetic acid.

Treatment of Ring I with $I_2$ in acetic acid results in the removal of the Acm protecting groups from Cys sulfhydryl groups and the formation of Rings II and II by the oxidation of the sulfhydryl groups to form a disulfide bond. The final product is purified on Sephadex eluted with 50% aqueous acetic acid and on Sephadex eluted with 2N aqueous acetic acid.

The following Examples illustrate methods of carrying out the present invention, but is to be understood that these Examples are given for purposes of illustration and not of limitation.

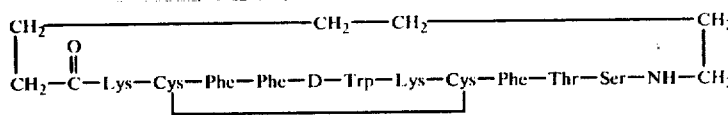

General Scheme for Preparing

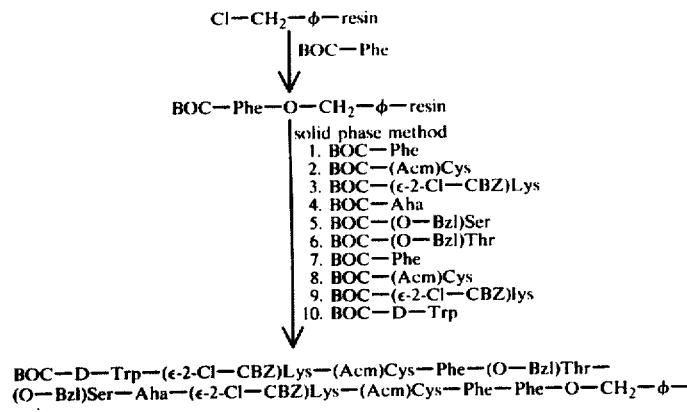

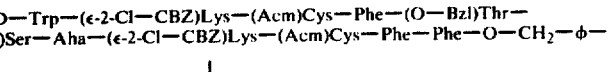

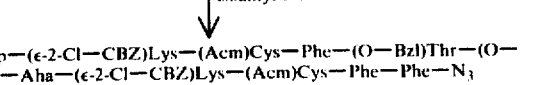

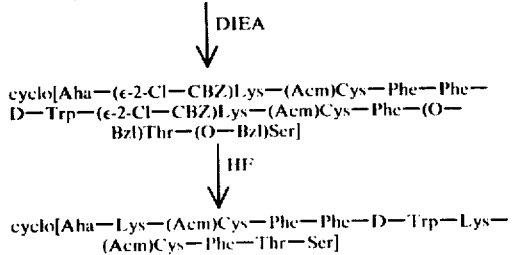

-continued

General Scheme for Preparing

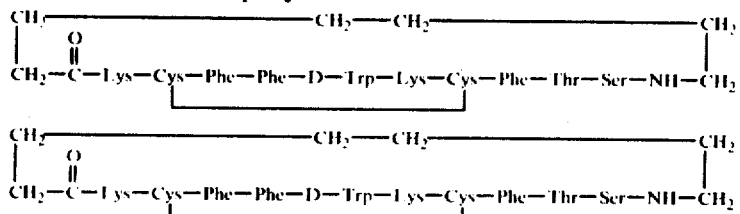

EXAMPLE 1

Preparation of

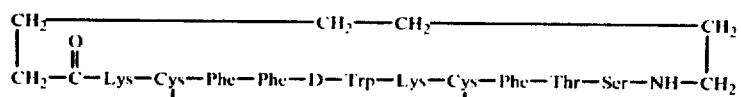

Step a) — Preparation of
D-Trp(ε-2-Cl-CBZ)Lys-(Acm)Cys-Phe-(O-Bzl)Thr-(O-Bzl)Ser-Aha-(ε-2-Cl-CBZ)Lys-(Acm)Cys-Phe-Phe-O-CH$_2$-φ-resin Chloromethyl resin (2% cross-linked Merrifield resin), 862.0 g. (2.37 moles), having 2.75 meq. chlorine/g., and 607.0 g. (2.37 moles, 1 equivalent) of BOC-Phe were added to 4320 ml. of peroxide-free tetrahydrofuran. The mixture was stirred in an oil bath at 80° C. bath temperature for 45 minutes. Triethylamine, 310.0 ml., was added and the reaction mixture stirred at 80° C. bath temperature for 70 hours, cooled to 25° C. and transferred to a stirred solid phase reaction column with 2000 ml. of tetrahydrofuran. After removal of the solvent, the resin was washed using the stirred column with:

3 × 2000 ml. of tetrahydrofuran
4 × 5170 ml. of ethanol
1 × 5170 ml. of acetic acid
3 × 5170 ml. of water
3 × 5170 ml. of methanol
3 × 5170 ml. of chloroform.

The BOC-Phe-O-CH$_2$-φ-resin was dried in vacuo at 25° C. for 16 hours, giving 1203 g. of BOC-Phe-O-CH$_2$-φ-resin containing 0.937 mmole of phenylalanine/g. of resin.

BOC-Phe-O-CH$_2$-φ-resin (2.13 g.; 2.0 mmole) was carried through the procedures in Tables III and IV using 2 deblockings (2 minutes and 25 minutes) with 25% TFA in methylene chloride in the presence of 1% ethanedithiol (except when deblocking BOC-Phe-O-CH$_2$-φ-resin), and 2.5 equivalents of BOC-amino acid in the required sequence until the desired BOC-undecapeptide-O-CH$_2$-φ-resin was obtained.

DCCI was used as the sole coupling agent in every step except the coupling of BOC-(O-Bzl)Ser to Aha-(ε-2-Cl-CBZ)Lys-(Acm)Cys-Phe-Phe-O-CH$_2$-φ-resin in which case the coupling was carried out with DCCI in the presence of 1-hydroxybenzotriazole monohydrate (HBT·H$_2$O).

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr and Ser was blocked with Bzl; the ε-amino group of Lys with 2-Cl-CBZ and the sulfhydryl group of Cys with Acm.

When the desired BOC-undecapeptide-O-CH$_2$-φ-resin was obtained, the N-terminal BOC group was removed by the terminal deblocking procedure set forth in Table V.

TABLE III

| Solvent or reagent (number of treatments or washes) | CHCl$_3$ (2) | 25% TFA in CH$_2$Cl$_2$ + 1% ethanedithiol (2)* | CHCl$_3$ (3) | NEt$_3$-CH$_2$Cl$_2$ (1:9) (2) | CHCl$_3$ (3) CH$_2$Cl$_2$ (3) | BOC AA in CH$_2$Cl$_2$, DMF or a mixture of both | 0.5M DCCI in CH$_2$Cl$_2$ | DMF (1) MeOH (1) DMF (1) MeOH (1) CHCl$_3$ (2) |
|---|---|---|---|---|---|---|---|---|
| Volume in ml. | 40 | 40 | 40 | 40 | 40 | 25 | 10 | 40 |
| Time in min. | 5 | 2 and 25 | 2 | 5 and 5 | 2 | 5 | 5 coupling 30 | 2 |

*1% ethanedithiol is present except in the deblocking of BOC-Phe-O-CH$_2$-φ-resin

TABLE IV

| Protected Amino Acid | Solvent ml. |
|---|---|
| BOC—Phe (1.33 g.) recouple | CH$_2$Cl$_2$, 25 ml. |
| BOC-(Acm)Cys (1.46 g.) recouple | DMF, 5 ml. CH$_2$Cl$_2$, 20 ml. |
| BOC-(ε-2-Cl—CBZ)Lys (2.08 g.) recouple | CH$_2$Cl$_2$, 25 ml. |
| BOC-Aha (1.23 g.) recouple | CH$_2$Cl$_2$, 25 ml. |
| BOC-(O-Bzl)Ser (1.48 g.) + |  |

TABLE IV-continued

| Protected Amino Acid | Solvent ml. |
|---|---|
| HBT . H₂O (1.53 g.) recouple | DMF, 25 ml. |
| BOC—(O—Bzl)Thr (1.55 g.) recouple | CH₂Cl₂, 25 ml. |
| BOC—Phe (1.33 g.) recouple | CH₂Cl₂, 25 ml. |
| BOC—(Acm)Cys (1.46 g.) | DMF, 5 ml. CH₂Cl₂, 20 ml. |
| recouple BOC—(ε-2-Cl—CBZ)Lys (2.08 g.) recouple | CH₂Cl₂, 25 ml. |
| BOC—D—Trp (1.52 g.) recouple | DMF, 5.5 ml. CH₂Cl₂, 19.5 ml. |

TABLE V
TERMINAL DEBLOCKING PROGRAM

| Solvent or reagent (number of treatments or washes) | CHCl₃ (1) | 25% TFA in CH₂Cl₂ + 1% Ethanedithiol (2) | CHCl₃ (3) | MeOH (2) CH₂Cl₂ (1) MeOH (2) CH₂Cl₂ (2) |
|---|---|---|---|---|
| Vol. in ml. | 40 | 40 | 40 | 40 |
| Time in minutes | 5 | 2 and 25 | 2 | 2 |

After the procedures of Tables III, IV and V were completed, the blocked undecapeptide-O-CH₂-φ-resin was dried overnight in vacuo and weighed 4.80 g.

Step b) — Preparation of D-Trp-(ε-2-Cl-CBZ)Lys-(Acm)Cys-Phe-(O-Bzl)Thr-(O-Bzl)Ser-Aha-(ε-2-Cl-CBZ)Lys-(Acm)Cys-Phe-Phe-NH-NH₂

To a mixture of 4.62 g. D-Trp-(ε-2-Cl-CBZ)Lys-(Acm)Cys-Phe-(O-Bzl)Thr-(O-Bzl)Ser-Aha-(ε-2-Cl-CBZ)Lys-(Acm)Cys-Phe-Phe-O-CH₂-φ-resin in 46 ml. freshly degassed DMF was added 4.62 ml. NH₂-NH₂. The mixture was magnetically stirred at room temperature for 1 hour. The mixture was filtered to remove the resin. The resin was washed with 4 × 10 ml. DMF. The filtrate and washings were concentrated in vacuo to near dryness. The semi-solid residue was triturated with 50 ml. water to obtain a solid. The solid was collected by filtration, slurried with 4 × 30 ml. water and dried in vacuo overnight to yield 2.90 g. crude product.

Step c) — Preparation of D-Trp-(ε-2-Cl-CBZ)Lys-(Acm)Cys-Phe-(O-Bzl)Thr-(O-Bzl)Ser-Aha-(ε-2-Cl-CBZ)Lys-(Acm)Cys-Phe-Phe-N₃

D-Trp-(ε-2-Cl-CBZ)Lys-(Acm)Cys-Phe-(O-Bzl)Thr-(O-Bzl)Ser-Aha-(ε-2-Cl-CBZ)Lys-(Acm)Cys-Phe-Phe-NH-NH₂ (2.88 g., 1.37 mmole), prepared by the process set forth in Step b), was suspended in 29 ml. freshly degassed DMF. The suspension was stirred magnetically at −25° C. To the suspension was added 1.3 ml. of 5.24N HCl in THF (6.9 mmole, 5 equivalents). To the resulting suspension, "pH" 1.5 to 2.0, was added 280λ isoamyl nitrite (2.09 mmole) and stirring continued until all the starting material dissolved. This solution of D-Trp-(ε-2-Cl-CBZ)Lys-(Acm)Cys-Phe-(O-Bzl)Thr-(O-Bzl)Ser-Aha-(ε-2-Cl-CBZ)Lys-(Acm)Cys-Phe-Phe-N₃ was used immediately in Step d).

Step d) — Preparation of Cyclo[Aha-(ε-2-Cl-CBZ)Lys-(Acm)Cys-Phe-Phe-D-Trp-(ε-2-Cl-CBZ)Lys-(Acm)Cys-Phe-(O-Bzl)-Thr-(O-Bzl)Ser]

The solution of D-Trp-(ε-2-Cl-CBZ)Lys-(Acm)Cys-Phe-(O-Bzl)Thr-(O-Bzl)Ser-Aha-(ε-2-Cl-CBZ)Lys-(Acm)Cys-Phe-Phe-N₃ in DMF, obtained by the process set forth in Step c), was diluted in 2850 ml. freshly degassed DMF, precooled to −40° C. The "pH" was adjusted to 7.2 to 7.6 by the addition of 6.0 ml. N,N-diisopropylethylamine and the solution maintained at −18° C. for 1 day and at 5° C. for 3 days.

The solution was concentrated in vacuo to near dryness. The residue was triturated with water to give a solid. The solid was collected by filtration, slurried with water (4 × 20 ml.) and dried in vacuo overnight to give 2.81 g. of product.

Step e) — Preparation of Cyclo[Aha-Lys-(Acm)Cys-Phe-Phe-D-Trp-Lys-(Acm)Cys-Phe-Thr-Ser]

Cyclo[Aha-(ε-2-Cl-CBZ)Lys-(Acm)Cys-Phe-Phe-D-Trp-(ε-2-Cl-CBZ)Lys-(Acm)Cys-Phe-(O-Bzl)Thr-(O-Bzl)Ser] 2.81 g., obtained by the process set forth in Step d), was dissolved in 5.6 ml. anisole and 56 ml. hydrogen fluoride at dry ice-acetone bath temperature. The solution was stirred magnetically at ice-bath temperature for 1 hour. The excess hydrogen fluoride was removed in vacuo at ice-bath temperature. The resulting oily residue was triturated with 35 ml. ethyl acetate to give a solid. The solid was collected by centrifugation, washed with 3 × 35 ml. ethyl acetate and dried in vacuo to give 2.39 g. of product.

Step f) — Purification of Cyclo[Aha-Lys-(Acm)Cys-Phe-Phe-D-Trp-Lys-(Acm)Cys-Phe-Thr-Ser]

The cyclo[Aha-Lys-(Acm)Cys-Phe-Phe-D-Trp-Lys-(Acm)Cys-Phe-Thr-Ser], 2.33 g., obtained by the process set forth in Step e), was dissolved in 25 ml. 50% aqueous acetic acid and charged to a column of Sephadex G-25, (5 cm.×115 cm., 2260 ml.) packed in 50% aqueous acetic acid. The column was eluted with 50% aqueous acetic acid at the rate of 1 ml./min. Fractions of 18.7 ml. were collected. The effluent was monitered at 254 nm.

Fractions 65 to 83 were combined, concentrated to dryness in vacuo and the residue lyophilized from 30 ml. 10% aqueous acetic acid to give 1.6905 g. of substantially pure product.

Step g) — Preparation of

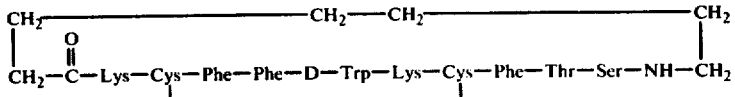

To a solution of 2.19 g. I₂ in 1000 ml. acetic acid was added a solution of 1.0 g. (0.646 mmole) cyclo-[Aha-Lys-(Acm)Cys-Phe-Phe-D-Trp-Lys-(Acm)Cys-Phe-Thr-Ser] in 25 ml. water and 100 ml. acetic acid. The resulting solution was stirred at room temperature for 5 hours. The reaction solution (less 100 ml.) was treated with 42 ml. 1N Na₂S₂O₃ and concentrated in vacuo to near dryness. To the residue was added 30 ml. 50% acetic acid and an additional 3 ml. 1N Na₂S₂O₃. The insoluble material was removed by filtration. The filter cake was washed with a total of 20 ml. 50% acetic acid. The combined filtrate and washings were charged to a column of Sephadex G-25, (5 cm. · 115 cm., 2260 ml.) packed in 50% aqueous acetic acid. The column was eluted with 50% aqueous acetic acid and fractions of 18.7 ml. were collected. The effluent was monitored at 254 nm.

Fractions 65 to 75 were combined, concentrated to dryness in vacuo and the residue was dissolved in 25 ml. 2N acetic acid and charged to a 5 cm. × 115 cm. column packed with Sephadex G-25 in 2N acetic acid and eluted with 2N acetic acid. The effluent was monitored at 254 nm. and 18.7 ml. fractions were collected.

Fractions 98 to 103 were combined, concentrated to dryness in vacuo and the residue lyophilized from 30 ml. 10% aqueous acetic acid to give 257.5 mg. of substantially pure product. A 20 hour toluenesulfonic acid hydrolysate showed the following amino acid analysis:

|  | μmole/mg. | normalized to Phe |
|---|---|---|
| Lys | 0.394 | 2.15 |
| Thr | 0.177 | 0.97 |
| Ser | 0.182 | 1.00 |
| Cys | 0.389 | 2.13 |
| Phe | 0.550 | 3.00 |
| Trp | 0.167 | 0.91 |

Inhibition of Insulin — Inhibition of Glucagon

The relative potencies of somatostatin analogs on the lowering of plasma insulin and glucagon are determined by the following method:

Analogs of somatostatin were combined to somatostatin in their ability to lower the levels of portal vein glucagon and insulin in anesthetized rats. Male Sprague-Dawley rats (Charles River CD) weighing 160-200 grams were anesthetized with urethane (150 mg./100 gm.) Saline or peptides were administered via the external jugular vein. After 5 minutes the portal vein was exposed and blood was collected via syringes containing 3 mg. EDTA and placed in chilled tubes containing 100 μl. of Trasylol (obtained from FBA Pharmaceuticals) for subsequent hormone analysis. Plasma levels of glucagon were determined by the method of Faloona, G. R., and Unger, R. H. "Glucagon" in Methods of Hormone Radioimmunoassay, eds. Jaffe, B. M. And Behrman, H. R. (Academic Press, Inc., New York) Chap. 18 pp. 317-330 (1974) utilizing glucagon antisera 30K. Plasma levels of insulin were determined by a modification of the procedure of Herbert, V., Lau, K. S., Gottlieb, C. W. and Bleicher, S. J., (J. Clin. Endocrin. and Metab.) 25, 1375-1384 (1965).

Inhibition of Pentobarbital Stimulated Growth Hormone Release In Vivo

Somatostatin analogs were compared to somatostain in their ability to inhibit the release of growth hormone in pentobarbital stimulated rats; a modification of the procedure of Brazeau et al. Endocrinology, 94, 184-187 (1974) was empaloyed. Rats were lightly etherized and sodium pentobarbitol (17 mg./Kg.) was injected into the exposed Saphenous vein; somatostatin or analog was simultaneously injected subcutaneously. After 15 minutes the animals were bled via the orbital sinus and blood collected for subsequent growth hormone analysis.

Growth Hormone Inhibition In Vitro

Rat pituicytes were isolated according to the procedures of Vale and Grant "In vitro Pituitary Hormone Secretion Assay for Hypophysiotropic Substances" in Methods in Enzymology. Vo. XXXVII, eds. O'Malley, B. W. and Hardman, J. G. (Academic Press, Inc., New York) pp. 5-93 (1975).

After 4 days in culture, the cells were washed and incubated for 4 hours in Dulbecco-modified Eagle's medium in the presence or absence of graded doses of each analog or somatostatin. The medium was then collected for subsequent growth hormone determination by a double antibody radioimmunoassay for rat growth hormone.

Statistical Analysis:

Doses were randomized between groups of animals (6 rats/group). Potency values were determined by four, six, or 8 point bioassays with somatostatin as the reference standard. Relative potency values were calculated by a relative potency formula for parallel line bioassays as described in Finney, D. J. Statistical Method in Biological Assay (Charles Griffin and Co., Ltd., London) Chap. 4 pp. 99-138 (1964). The results are as follows:

ACTIVITY OF SELECTED ANALOGS: POTENCY RELATIVE TO SOMATOSTATIN

| Compound | Inhibition Of Insulin | Inhibition Of Glucagon | Inhibition of Pentobarbital Stimulated Growth Hormone Release In Vivo | Growth Hormone Inhibition In Vitro |
|---|---|---|---|---|
| Somatostatin | 1 | 1 | 1 | 1 |
| cyclo(Aha—Lys—Cys—Phe—Phe—D—Trp—Lys—Cys—Phe—Thr—Ser) | 0.06 (0.03–0.11) | <0.1 | 0.5 (0.2–1.1), 0.2 (0.1–0.8) | 0.06 (0.03–0.10), 0.08 (0.03–0.18), 0.2 (0.1–0.3) |
| cyclo(Aha—Lys—Cys—Phe—Phe—D—Trp—Lys—Cys—Phe—Thr—Ser), Acm, Acm | 0.58 (0.25–1.22) | 0.29 (0.03–1.03) | 0.5 (0.2–1.3) | 0.15 (0.11–0.22) |

Effect of Somatostatin Analogs on Gastric Secretion

The effect of somatostatin and its analogs on gastric secretion were determined by the following method:

Compounds were tested for their ability to inhibit pentagastrin evoked gastric secretion in the chronic fistula dog. Female beagle dogs with a chronic gastric fistula were given pentagastrin (2.5 μg./kg./hour, i.v. from −60 to 120 min.) and gastric outputs were collected via the fistula cannula. Samples were analyzed at 30 minute intervals for volume (ml.) and titratable acid (mEq/L) (titration to pH 7 with 0.01N NaOH); total acid output (mEq) was calculated as the production of output volume and acid concentration. Test compounds were infused at a constant rate from 0 to 60 minutes. Data have been expressed as percent change of total acid output relative to a placebo trial in the same animals.

The results are as follows:

0.00142 mg. to about 0.428 mg./kg. of body weight administered by intravenous infusion or by subcutaneous injection. The required dosage will vary with the particular condition being treated, the severity of the condition and the duration of treatment.

If the active ingredient is administered in tablet form, the tablet may contain: a binder such as gum tragacanth, corn starch, gelatin, an excipient such as dicalcium phosphate; a disintegrating agent such as corn starch, and alginic acid; a lubricant such as magnesium stearate; and a sweetening and/or flavoring agent such as sucrose, lactose and wintergreen. Suitable liquid carriers for intravenous administration include sterile water, isotonic saline and phosphate buffer solutions or other pharmaceutically acceptable injectable carriers.

The following example is included to illustrate the preparation of a representative dose of

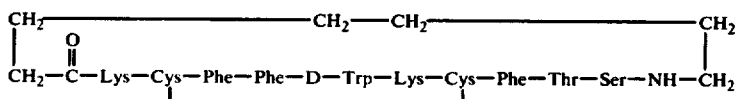

suitable for subcutaneous injection.

| Effect of Somatostatin Analogs on Gastric Secretion (Dose 0.8 μg./kg./min.; 0-60 min.) | | | | | |
|---|---|---|---|---|---|
| | PERCENT CHANGE TOTAL ACID OUTPUT | | | | |
| Compound | 0-30 | 30-60 | 60-90 | 90-120 | (N) |
| cyclo(Aha—Lys—Cys—Phe—Phe—D—Trp—Lys—Cys—Phe—Thr—Ser)<br>            Acm                                         Acm | +21 | +45 | +80 | +64 | (2) |
| cyclo(Aha—Lys—Cys—Phe—Phe—D—Trp—Lys—Cys—Phe—Thr—Ser) | −44 | +11 | −14 | +8 | (2) |

The somatostatin analogs of the present invention and the non-toxic pharmaceutically acceptable salts thereof, are useful in humans and animals for inhibiting growth hormone release as in the treatment of acromegaly without affecting the level of gastric secretions or without affecting the level of gastric secretion, insulin and glucagon. These analogs are particularly useful in the treatment of diabetic retinopathy. In the treatment of acromegaly and diabetic retinopathy, the number and size of daily doses and the time of administration are determined by an individual study of each subject. The method of determining these factors is known to those skilled in the art.

The somatostatin analogs described herein may be administered to warm blooded animals, including humans, either intravenously, subcutaneously, intramuscularly or orally. The contemplated dose range for oral administration in table or capsule form to large mammals is about 0.001 mg. to about 7 mg./kg. of body weight per day. These somatostatin analogs are preferably administered by injection. A therapeutically effective amount of an analog is ordinarily supplied at a dosage level of from about 0.001 mg. to about 2 mg./kg. of body weight. Preferably the range is from about

EXAMPLE 2

1 ml. sterile saline;
1 mg.

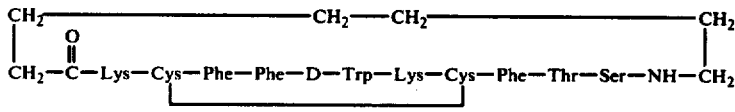

What is claimed is:

1. The compounds having the formula:

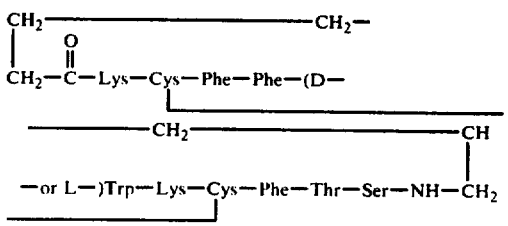

and pharmaceutically acceptable non-toxic acid addition salts thereof.

2. The compounds having the formula:

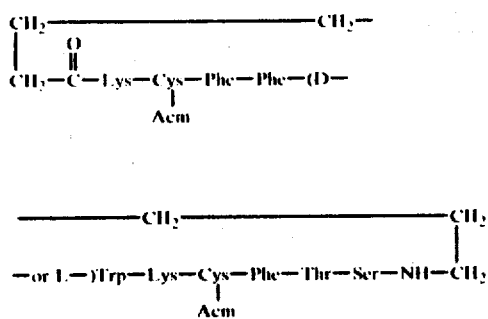
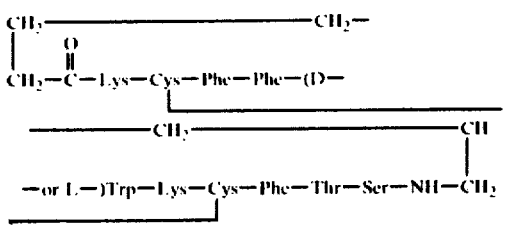
3. A pharmaceutical composition comprising a therapeutically effective amount of the peptide having the structure:
and non-toxic acid addition salts thereof in a pharmaceutically acceptable liquid or solid carrier thereof.
* * * * *